United States Patent [19]
Klemp

[11] Patent Number: 5,595,709
[45] Date of Patent: Jan. 21, 1997

[54] INSTRUMENT FOR MEASURING NON-METHANE ORGANIC GASES IN GAS SAMPLES

[75] Inventor: Mark A. Klemp, Swartz Creek, Mich.

[73] Assignee: Chromatofast, Ann Arbor, Mich.

[21] Appl. No.: 237,453

[22] Filed: May 3, 1994

Related U.S. Application Data

[63] Continuation-in-part of Ser. No. 938,812, Sep. 1, 1992, abandoned.

[51] Int. Cl.[6] ................................................. G01N 30/00
[52] U.S. Cl. ........................... 422/88; 422/94; 436/143; 436/141; 436/177; 436/178; 436/154; 73/23.31; 73/23.39; 73/31.07; 73/863.12
[58] Field of Search ................................. 73/23.35, 23.31, 73/23.2, 23.4, 23.39, 31.05, 31.07, 863.12; 422/88, 94, 98, 54; 436/139, 141, 143, 154, 177, 178, 181; 95/141, 87, 88; 96/101, 100

[56] References Cited

U.S. PATENT DOCUMENTS

| | | | |
|---|---|---|---|
| 3,444,722 | 5/1969 | Roof | 73/23.39 |
| 3,762,878 | 10/1973 | Villalobos | 73/23.39 |
| 4,003,257 | 1/1977 | Fletcher et al. | 73/19.02 |
| 4,042,332 | 8/1977 | Saitoh et al. | 436/175 |
| 4,302,422 | 11/1981 | Takahashi | 73/23.39 |
| 4,576,918 | 3/1986 | Yeung | 436/179 |
| 4,805,441 | 2/1989 | Sides et al. | 73/23.39 |
| 4,962,042 | 10/1990 | Morabito et al. | 422/89 |
| 5,037,795 | 8/1991 | Wieserman et al. | 95/88 |
| 5,073,666 | 12/1991 | Zemanian et al. | 585/500 |
| 5,171,921 | 12/1992 | Gaffney et al. | 585/653 |
| 5,411,707 | 5/1995 | Hiatt | 422/89 |

Primary Examiner—Robert J. Warden
Assistant Examiner—Hien Tran
Attorney, Agent, or Firm—Harness, Dickey & Pierce, PLC.

[57] ABSTRACT

An analytical system for measuring the concentration of non-methane organic gases within a test sample including methane and non-methane component groups. In one version, a dual column analysis system utilizes a metal column and a porous layer open tubular (PLOT) column to separate methane and non-methane organic gases (NMOG). The metal column captures non-methane compounds which are more easily thermally trapped on the metal column, generally higher molecular weight compounds and polar molecule, which prevents these compounds from contaminating the PLOT column. In another version, the system incorporates a single trap in the form of a porous layer open tubular (PLOT) column which the sample mixture is directed through and which traps the NMOG group through adsorption. The methane group passes through the trap and is vented to atmosphere or evaluated using a detector. After trapping of the NMOG group, the flow direction through the column is reversed and the column temperature is increased to desorb the NMOG group which is evaluated using a detector such as a flame ionization detector (FID).

6 Claims, 2 Drawing Sheets

INSTRUMENT FOR MEASURING NON-METHANE ORGANIC GASES IN GAS SAMPLES

CROSS REFERENCE TO RELATED APPLICATION

This application is a continuation-in-part of U.S. application Ser. No. 938,812, filed Sep. 1, 1992 now abandoned.

FIELD OF THE INVENTION

This invention relates to an organic compound analytical instrument, and in particular, to one capable of providing a measurement of the concentration of non-methane organic gases (NMOG) in samples containing methane such as internal combustion engine exhaust gases.

BACKGROUND OF THE INVENTION

Those concerned with environmental emissions from sources such as internal combustion engines are often interested in quantifying the total concentration of certain compounds within the exhaust gas. In some evaluations, rather than requiring speciation of the mixture, the total concentration of NMOG emissions as a lumped parameter is desired. The distinction between methane and NMOG relates to differences in environmental impact attributed to these different groups of gases.

Various techniques are currently used for determining NMOG concentrations. One approach obtains the value of NMOG as a difference in the measurements of total hydrocarbons and methane using a flame ionization detector (FID). Several problems are associated with the current test methods. As methane can be a significant proportion of exhaust composition, small errors in the measurement of either methane or total hydrocarbon levels result in large errors in the estimation of NMOG levels. In fact, it is not uncommon for this evaluation technique to result in yields of negative NMOG emissions. In addition, the current method requires large volumes of dilution air to be mixed with the exhaust gas, and samples are stored in so-called "Tedlar" sample bags before analysis. The purpose of dilution air is to prevent significant water condensation on the walls of the Tedlar bags. The use of Tedlar bags is problematic with certain compounds found in exhaust gas, and it has been found that the dilution air can have levels of NMOG exceeding that found in the raw gas under certain circumstances. The use of Tedlar bags further raises concerns with the test reliability, reproducability and stability, and provides a media for adsorption and interactions of certain compounds. Particularly in the case of oxygenated organic compounds, reactivity with the walls of the Tedlar bags is a known problem. Moreover, current processes are very time consuming to carry out, which is a particular disadvantage in engine development applications.

The accuracy limitations of current procedures for NMOG determination are especially of concern in view of increasingly stringent vehicle emission requirements. Legislation by the Federal Government (Federal Clean Air Act) and the California Air Research Board (CARB) have defined further limitations on vehicle emissions to improve air quality. These new mandates require that vehicles sold must be designed to meet stringent emissions standards which are a fraction of the presently accepted levels. In addition to evaluating regulatory compliance, instruments for NMOG determination can be used by automotive manufacturers while developing their products.

Other evaluation procedures have been proposed and considered for methane and NMOG measurement using a trap in which NMOG components are collected and later desorbed for evaluation using an FID. In one device, a packed column for adsorbing NMOG components is used to separate out the methane, and thereafter, the trapped NMOG is desorbed. Traps based on adsorption, however, have the disadvantage of having a long desorption time which lengthens measurement time and limits accuracy due to the difficulty in integrating the output.

SUMMARY OF THE INVENTION

In view of the foregoing, there is a need for an analytical instrument which provides a fast and accurate measurement of NMOG concentrations. The instrument in accordance with this invention provides such evaluation within several seconds rather than tens of minutes as in the case of prior art devices. The instrument of this invention further provides a means of direct sampling which eliminates the need for sample collection bags and large volumes of dilution air. The instrument of this invention operates on the basis of a single trap or pair of traps which enables separation of methane from NMOG.

In the preferred embodiment of this invention, a dual column trap system is used having a metal capillary tube trap and a series connected porous layer open tubular (PLOT) trap for separating methane and non-methane organic gases (NMOG). The metal column traps generally higher molecular weight material which are readily thermally trapped, and the PLOT column passes methane gases while trapping the remaining non-methane gases. As a result, water and higher boiling point molecules are trapped and prevented from contaminating the PLOT column which extends its life and reduces trapping cycle time.

Both columns trap and release their respective gases in response to regulation of their temperatures. The metal column uses thermal cryofocusing to thermally trap and desorb gases, whereas the PLOT column thermally and chemically adsorbs and desorbs gases. By forward flushing the PLOT column into a detector while at a trapping temperature, the methane gas group which passes through can be evaluated using the detector, and the trapped non-methane gases adsorbed in the PLOT column can be desorbed and forward flushed from the column by increasing the column temperature. As a result, the detector produces a pair of humps, one from the methane gas group which is directly passed and the other from the adsorbed/desorbed component of the non-methane gas group. Likewise, the metal column is backflushed with a carrier gas while the column is thermally heated which desorbs the trapped component of the non-methane gas group which is then carried to a respective detector where it is evaluated. By separating the pair of "humps" measured from the PLOT column, the output of the first produced hump formed by directly passed methane gases can be integrated to quantify the methane gases passed through the PLOT column. Likewise, by integrating the non-methane gas group trapped in the metal column, and adding it to the remaining integrated output of non-methane gases trapped in the PLOT column, namely the second hump, a quantitative evaluation of the concentration of NMOG components is provided.

In an alternative embodiment of this invention, the separator comprises a single PLOT column trap tube which, when held at or below ambient temperature, permits a group of gases including methane to pass through the column whereas a second group of NMOG components are adsorbed within the column. The unseparated methane gas group can be evaluated using a detector such as an FID or can be vented. After the methane gas group has been transported through the column, fluid flow direction through the column is reversed and the column temperature is increased, causing the retained NMOG to be desorbed and directed through a detector such as an FID. By integrating the output of the detector over time, a quantitative evaluation of the concentration of NMOG components is provided.

Additional benefits and advantages of the present invention will become apparent to those skilled in the art to which this invention relates from the subsequent description of the preferred embodiments and the appended claims, taken in conjunction with the accompanying drawings.

DETAILED DESCRIPTION OF THE INVENTION

A. First Preferred Embodiment

Figure 1:
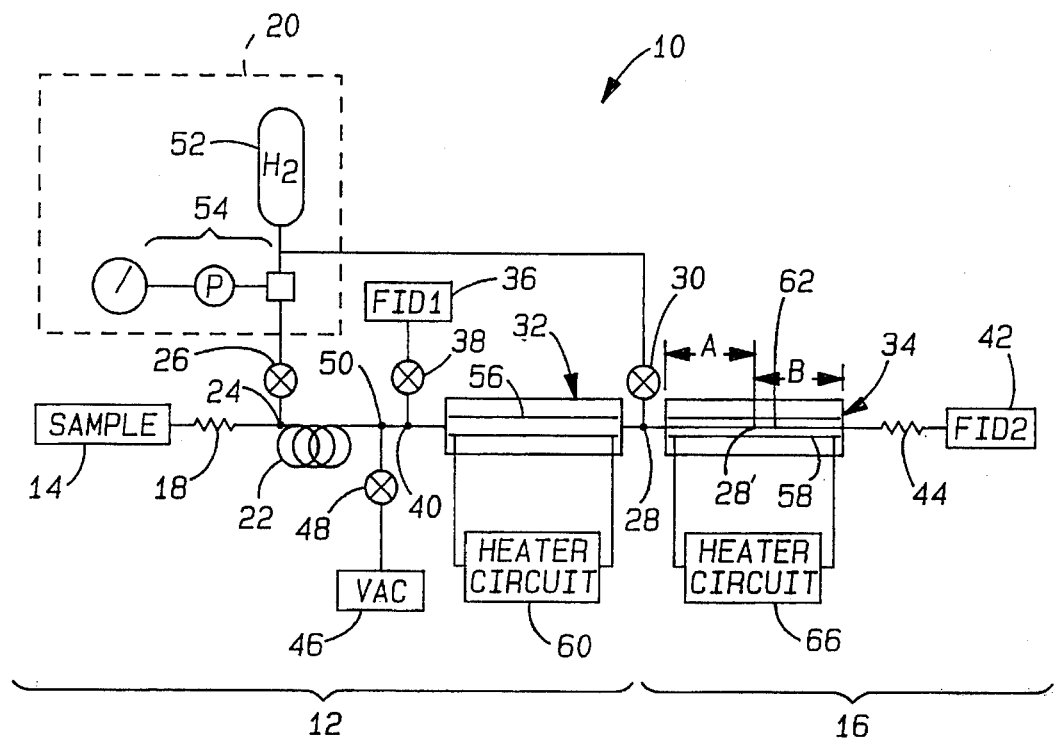
FIG. 1 is a schematic illustration of an analysis instrument in accordance with a preferred embodiment of this invention.

An analysis system in accordance with a first preferred embodiment of this invention is shown schematically in FIG. 1 and is further designated by reference numeral 10. In FIG. 1, solid lines interconnecting pairs of system elements indicate fluid flow conduits. Dual column analysis system 10 separates and measures concentrations of a non-methane organic gases group and a methane gases group from a gas sample utilizing a dual column tap technique. The system 10 includes a first branch 12 of fluid flow elements, generally shown on the left-hand side of FIG. 1, with a second branch 16 at the right-hand side of FIG. 1. A sample source 14 is included in first branch 12 where it is connected in conduit flow such that a sample is introduced into the conduit for evaluation.

Typically, the sample source is an internal combustion engine such that an exhaust outlet on the engine is interconnected to first branch 12. Sample source 14 is connected to a fluid restrictor 18 which is provided to produce flow restriction through the system which adjusts fluid flow rates between various branches therethrough. A carrier gas source 20 supplying a gas such as hydrogen is connected at a first location between restrictor 18 and sample gas storage loop 22 at a tee connector 24 through an on/off valve 26, and a second location between the first and second branches 12 and 16 at a tee connector 28 through an on/off valve 30. A metal trap 32 is connected to an end of first branch 12 opposite the sample source 14. Likewise, a PLOT trap 34 is provided at one end of second branch 16 such that first and second branches 12 and 16 are joined together at tee connector 28 by joining the metal trap 32 to the plot trap 34.

A detector which can be constructed in various forms but preferably is a flame ionization detector (FID) 36 is connected to first branch 12 by tee connector 40 on an opposite side of metal trap 32 from tee connector 28. A vacuum source 46 is connected to first branch 12 with an on/off valve 48 through a tee connector 50 which is provided between the sample loop 22 and tee connector 40. Furthermore, a second detector 42 which is preferably a flame ionization detector (FID) is connected to second branch 16 at an opposite end of the branch from tee connector 28 such that FID 42 is connected to PLOT trap 34 through a fluid restrictor 44.

Carrier gas source 20 provides a source of hydrogen (or other) carrier gas contained in a pressurized vessel 52 whose delivery pressure is monitored and regulated by a pressure meter and delivery valve 54 either to first branch 12 through tee connector 24 when valve 26 is open, or to both the first and second branches 12 and 16 at tee connector 28 when valve 30 is open. Valves 26 and 30 are selectively opened and closed to supply a carrier gas for moving a gas sample through the fluid flow elements of the system 10. Before applying the carrier gas, a gas sample is first delivered to sample loop 22 by applying a vacuum source 46 through valve 48 while valves 26, 30 and 38 are preferably closed. Then the carrier gas is selectively applied by sequentially activating such valves which moves the gas sample through the first and second branches of system 10 for analysis.

Metal trap 32 is formed from an elongated tubular column 56 which is preferably formed from stainless steel which selectively thermally traps a portion of non-methane organic gases group (NMOG), as well as water and water vapor, while permitting the remaining portion of non-methane gases, methane, and a group of so-called permanent gases (nitrogen, oxygen, carbon dioxide) to pass through the column into the PLOT trap 34. The temperature of the metal column is regulated to effect thermal cryofocusing while at a low temperature, and to desorb the cryofocused gases at a subsequently elevated temperature. Column 56 is connected to an electric heater circuit 60, preferably a capacitive discharge heater circuit, to form a heater tube which functions to controllably regulate the temperature of metal column 56 in order to selectively thermally trap and release selective non-methane organic gases and water, as will be described in more detail. The outlet end of column 56 is connected to second branch 16 by tee connector 28. By thermally regulating the temperature of metal column 56, certain non-methane organic gases are selectively thermally trapped in the column and remaining gases are passed therethrough into PLOT trap 34.

Trap 34 is formed from an elongated column of the porous layer open tubular (PLOT) type. PLOT column 62 has an inside coating of a stationary phase material such as aluminum oxide (A10) which adsorbs a group of gases referred to as NMOG, while permitting a second group of gases including methane and so-called permanent gases (nitrogen, oxygen, carbon dioxide) to pass through the column. Other PLOT column configurations and stationary phases could also be used, including the following commercially available products: PoraPLOT Q™, PoraPLOT U™, and CarboPLOT™ columns. PLOT column 62 is surrounded by a heater tube 58 which is connected to an electric heater circuit 66, which is also preferably a capacitive discharge heater circuit, which functions to regulate temperature of column 62 such that the column temperature is rapidly decreased to absorb NMOG and increased to desorb NMOG, as will be described in more detail. First end of PLOT column 62 receives gases through tee connector 28 whereas second end of column 62 is connected to a second flame ionization detector (FID) 42 through a fluid restrictor 44. Restrictor 44 serves to control fluid flow rates through PLOT column 62 and into FID 42. Carrier gas source 20 is connected between the metal column 56 and PLOT column 62 at tee connector through on/off valve 30.

An example of a dual column analysis system 10 would preferably employ the following specific components and parameters for the analysis of internal combustion engine exhaust gases:

| ELEMENT NUMBER | ELEMENT NAME | SPECIFICATION/ PARAMETER |
| --- | --- | --- |
| 18 and 44 | Restrictor | 0.1 mm fused silica glass capillary tubing, 30 cm long |
| 20 | Carrier Gas Source | Hydrogen |
| 26, 30, 38, 48 | Valves | Low dead-volume On/off solenoid controlled valves of the type commonly used in gas chromatography instruments |
| 56 | Metal Column | Stainless Steel Tubing |
| 62 | PLOT Column | 15 cm long fuse silica glass capillary, 0.32 mm ID with AlO stationary phase coating |
| 58 | Heater Tube | Stainless Steel Tubing |
| 60, 66 | Heater Circuit | Capacitive-Discharge circuit as described in U.S. Pat. No. 5,096,471, herein incorporated by reference |

In operation, a dual column analysis system 10 of this invention will operate in accordance with it's depiction as shown in FIG. 1 and described as follows. At the beginning of an analysis procedure, exhaust gas or some other type of gas sample is delivered for evaluation from sample source 14 into sample loop 22 by opening valve 48 while valves 26, 30 and 38 are closed. As a result, a vacuum is applied from vacuum source 46 through tee connector 50 such that a gas sample is pulled through restrictor 18 where it is delivered and stored in sample loop 22. Once the gas sample is received in loop 22, valve 48 is closed which retains the gas sample in the loop. Consequently, valve 26 is opened such that carrier gas source 20 drives the gas sample into and through metal column 32 while it is thermally held at a desirable "trapping" temperature such that higher boiling point molecules namely a group of non-methane organic gases and water, are thermally trapped on the metal column where they are retained, and the remaining methane gases group, and carrier gases are passed into PLOT column 62 where the remaining non-methane organic gases are adsorbed while the PLOT column is likewise retained at a temperature for effecting chemical adsorption of the non-methane in a PLOT column. As a result, the carrier gas delivers the gas sample through metal column 56 where a portion of the non-methane organic gases are retained, and the remaining gases are passed through PLOT column 62 where the remaining portions of non-methane organic gases are also adsorbed, and finally, gases of the methane group are passed therethrough such that they flow through restrictor 44 into FID 42 where their presence is detected and their quantity is measured.

The temperature of metal column 56 is set to allow a methane group of gases and portion of the non-methane organic gases to pass through the column when thermally regulated at a trapping temperature. This group of gases will generally have smaller molecular weight, and will typically be harder to thermally cryofocus, or trap, in the metal column. As a result, the methane group of gases and the non-methane organic gases which are not trapped in metal column 56 pass through the metal column into PLOT column 62. The remaining, generally higher molecular weight, NMOG will be thermally trapped in metal column 56. As the carrier gases drive the gas sample through the metal column and into PLOT column 62, the remaining non-methane organic gases are adsorbed in the PLOT column.

Accordingly, metal column 56 acts as a pre-separation column which thermally traps water, water vapor, and non-methane groups of gases which are more easily thermally trapped in the metal column. These trapped products are usually highly polar and typically comprise molecular chains of higher molecular weight which might otherwise contaminate and clog the PLOT column. By trapping these products in the metal column, it is easier to clean the PLOT column subsequent to extended use, and the life of the PLOT column is extended.

In order to provide adequate pre-separation, the temperature of column 56 is preferably held at a desirable "trapping" temperature which is within a predetermined range, and which is believed to extend from ambient temperatures (e.g. 20° C.) to sub-ambient temperatures down to −100° C. and perhaps lower, depending on the particular configuration of system 10 and especially column 56. Where an ambient trapping temperature is used, the trapping temperature can be provided by exposing column 56 to ambient air. Where cooler trapping temperatures are needed, in order to trap a desired range of non-methane gases, a bath of cool water or a cold gas (e.g. nitrogen) can be used to cool column 56.

Once the methane gas group and the remaining non-methane organic gas group which was not thermally trapped in the metal column 56 has passed through the column beyond tee connector 28, it is delivered into PLOT column 62 such that the PLOT column is held at a desirable adsorption temperature which adsorbs the remaining non-methane organic gases in the column. The methane gases group passes through the PLOT column through restrictor 44 and into FID 42 where their presence and concentration are measured and quantified. Once the methane gas group and remaining non-methane gases have passed tee connector 28, valve 30 is opened such that carrier gas source 20 is applied to tee connector 28. Valve 30 is opened in conjunction with the thermal modulation of both the metal column 56 and PLOT column 62 through respective heater circuits 60 and 66 which act on metal column 56 and heater tube 58, respectively. After operation, the tube forming column 56 and tube 58 are brought to an elevated temperature to desorb trapped gases in each respective column such that delivery of carrier gases at tee connector 28 delivers the desorbed gases in two directions through FID's 36 and 42, respectively. Upon opening valve 30, valve 38 is also opened while valves 48 and 26 remain closed. Restrictor 44 provides for a balanced split flow of carrier gases from the connector 28 into the metal column 56 and the PLOT column 62 such that thermally released gases are carried through valve 38 into FID 36 where the released NMOG concentration and quantity is measured. Likewise, carrier gases collect and deliver desorbed gases from PLOT column 62 through restrictor 44 and into FID 42 where corresponding gas concentration is measured.

Dual trap analysis system 10 provides a significant improvement in that metal column 56 is preferably tailored by adjusting column lengths and temperatures to thermally trap the heaviest components of the gas sample, typically those having molecular chains with five carbons or more, and the lighter components, typically those having molecular chains with four or less carbons, travel through the metal column to the PLOT column where the remaining non-methane gas group is chemically adsorbed through thermal regulation. Furthermore, an improvement is provided by supplying carrier gas at tee connector 28 such that only metal column 56 is subject to backflush of gases during the thermal release phase. As a result, gases trapped in metal column 56 are analyzed on FID 36, while gases adsorbed and gases passed through PLOT column 62 are measured or integrated on FID 42. Since PLOT column 62 is not backflushed in this procedure, flow through the PLOT column does not change, which provides a benefit of more consistent and enhanced chemical adsorption/desorption in response to thermal regulation. Furthermore, durability of the PLOT column 62 is improved since backflushing can seriously affect the life and durability of a PLOT column. Furthermore, metal column 56 traps the generally higher molecular weight carbon chain compounds of non-methane gas, i.e., those that are more easily thermally trapped in the metal column 56, such that they do not enter PLOT column 62 which makes clean-up of the PLOT column easier. Water is also prevented from entering PLOT column 62 as it is thermally trapped in the metal column 56. Additionally, use of the two column system allows for application of carrier gases through tee connector 28 in order to backflush of metal column 56 even before separation is completed in PLOT column 62. As a result, this system provides further advantages in speed when separating gases.

Once the methane gas group and the remaining non-methane gas group have passed through metal column 56 into PLOT column 34, carrier gas is supplied from source 20 to the tee connector 28 by opening valve 30, while valve 26 and 48 are closed, and valve 38 is opened. This action produces a split flow of carrier gas at tee connector 28 in which a fraction of the carrier gas backflushes through metal column 56 and a remaining portion continues to flow forward through PLOT column 62 through restrictor 44 and into FID 42 where its presence is detected and a quantitative measurement is provided.

Figure 2:
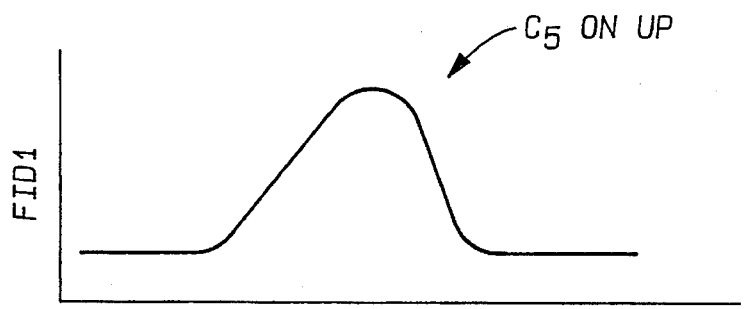
FIG. 2 is a representative chromatogram from a detector providing a partial measurement of NMOG concentration which is trapped in a metal trap using the instrument of FIG. 1.

FIG. 2 provides a representative output from FID 36 where the area under the curve can be integrated to obtain a measure of the concentration of the first part of the non-methane organic gas group trapped by metal column 56. Such gas group is backflushed through the metal column 56 where it is measured by FID 36. The balance of carrier gas received from carrier source 20 flows forward through PLOT column 62 while the PLOT column is held at a desirable thermally regulated desorption temperature such that a chemical desorption releases previously adsorbed non-methane gases from the PLOT column which are now carried through restrictor 44 and which are delivered through FID 42 where their presence is detected and a quantitative measurement is provided.

Figure 3:
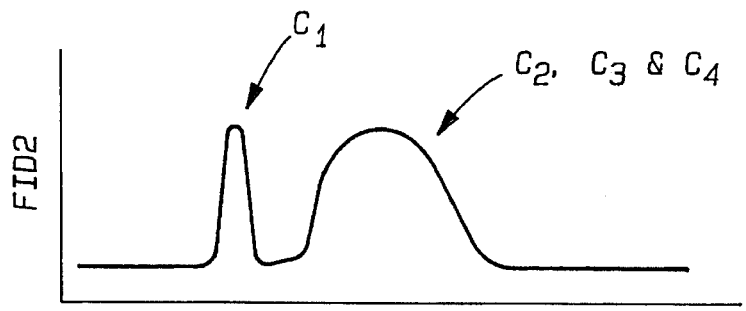
FIG. 3 is a representative chromatogram from a detector providing a measurement of methane concentration and a remaining partial measurement of NMOG concentration which is trapped in a PLOT trap using the instrument of FIG. 1.

FIG. 3 provides a representative output from FID 42 which comprises a pair of humps. The first hump results from methane which was directly passed through PLOT column 62 and the second hump represents non-methane organic gases which were adsorbed and desorbed in the PLOT column which delayed their being directly delivered to FID 42. By integrating the area under each hump, a measure of the concentration of the methane gases passed through PLOT column 62 can be obtained by measuring the area under the first hump, and the remaining measure of concentration of the non-methane gas group can be further obtained by measuring the area under the second hump.

By adding the area of the hump obtained from FID 36 as shown in FIG. 2, with the area of the second hump in FIG. 3, the total amount of non-methane organic gases (NMOG) can be quantified and obtained. Simultaneous with opening of valve 30, both heater circuits 60 and 66 are activated, causing the temperature of the tube forming column 56 and heater tube 58 to increase rapidly which subsequently increases the temperatures of metal column 56 and PLOT column 62 which causes the previously trapped and adsorbed gas in each column to be thermally released and desorbed, respectively, where they are subsequently both picked up by the carrier gas and delivered to FID 36 and FID 42, respectively. By opening valve 38, the portion of the NMOG components which are released from metal column 56 pass through FID 36 where they are detected and quantified by integrating their resulting output as depicted in FIG. 2.

FIG. 2 provides a representative output of the desorbed component of NMOG group measured by FID 36. The flow of carrier gases backward through metal column 56 also provides a backflushing which clears the column for subsequent sample evaluation. The forward flow of carrier gas through PLOT column 62 flushes desorbed remaining non-methane organic gases from the PLOT column which carries them through restrictor 44 through FID 42 for analysis and quantitative measurement. After methane and non-methane gases have been integrated at FID's 36 and 42, valves 26, 30, 38 and 48 are closed, which prepares the system 10 for receiving a new gas sample which is introduced from sample source 14 by opening valve 48.

It is to be understood that further variations of the preceding preferred embodiment will provide a device which functions essentially the same but with slightly modified structure. For example, FID 36 can be eliminated and tee connector 40 can be ported through valve 38 with a line which connects between PLOT trap 34 and fluid restrictor 44 such that valve 38 is opened during backflush of the metal trap 32 where the desorbed component of non-methane gases are analyzed with FID 42. Typically, such a modification would produce an output from FID 42 with three separate humps such that the first hump quantifies the component of methane gases present in a gas sample, and the remaining pair of humps quantify the component of non-methane gases present.

In operation, it is preferable to provide a carrier gas velocity which is at least 100 cm per/sec., a PLOT column and metal column having a combined maximum length of 30 cm, and a heating rate up to 100,000° C./sec. Furthermore, it is desirable to produce a FID signal output with humps having a base width, or base bandwidth, with a maximum of 10 milliseconds. Such a pulse requires rapid desorption from the PLOT column which can only be produced by rapidly thermally decreasing the temperature of a column. A wider pulse tends to be more difficult to integrate, especially with small sample sizes detected by the FID such that overlap may exist between the methane and non-methane components of gas as detected by the FID.

Alternatively, tee connector 28 can be formed within the PLOT column 34 along the PLOT column 62 as shown by tee connector 28' which is connected to valve 30 by a dash line indicating an alternative fluid flow element. Such an alternative arrangement for the tee connector 28' allows for backflushing of at least a portion of the PLOT column, and where tee connector 28' is provided downstream of the PLOT column, for complete backflushing of the PLOT column. In this case, the metal column 32 generally traps components which might contaminate the PLOT column 34, yet still provides for at least partial backflushing of the PLOT column in order to clean those contaminants not trapped in the metal column 32. As alternatively depicted in FIG. 1, tee connector 28' is positioned a distance A downstream of the inlet to the PLOT column 34, and a distance B from the downstream end of the PLOT column 34.

B. Second Preferred Embodiment

Figure 4:
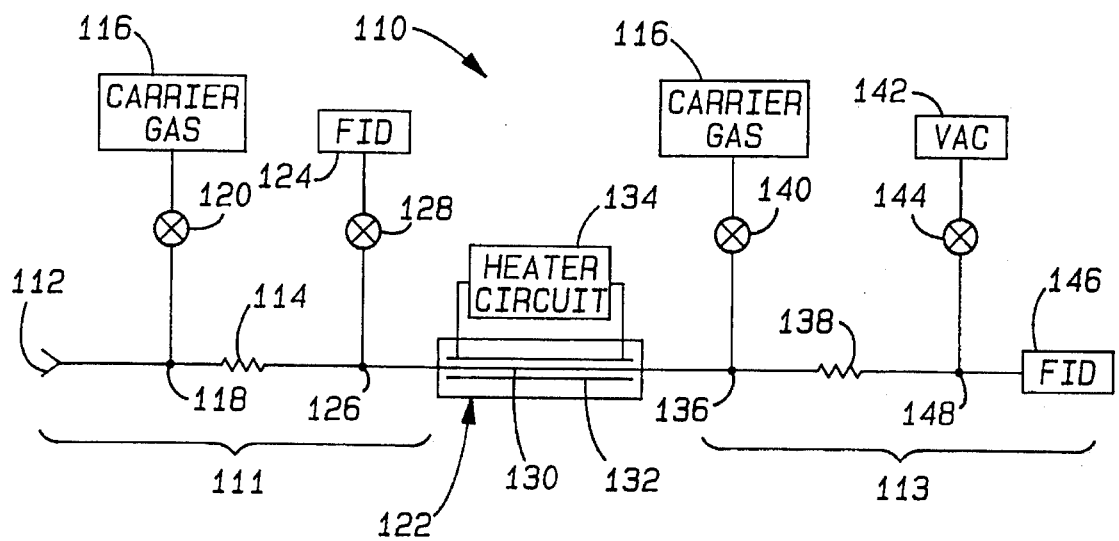
FIG. 4 is a schematic illustration of an analysis instrument in accordance with a second preferred embodiment of this invention.

An analysis system in accordance with this invention is shown in schematic fashion in FIG. 4 and is designated there by reference number 110. In the Figure, solid lines connecting system elements indicate fluid flow conduits. System 110 includes a first branch 111 of fluid flow elements on the left-hand side of the Figure, with a second branch 113 at the right-hand side of the Figure. First branch 111 includes sample inlet 112 which is the point at which a sample to be evaluated is introduced, such as internal combustion engine exhaust gases. Inlet 112 is connected to a fluid restrictor 114 which is provided for adjusting fluid flow rates through the system. A carrier gas source 116 supplying a gas such as hydrogen is connected between sample inlet 112 and restrictor 114 at tee connector 118 through on/off valve 120. First branch 111 is also connected to trap 122. A detector 124 which can take various forms but preferably is a flame ionization detector (FID) 124 is connected between restrictor 114 and trap 122 at tee connection 126. An on/off valve 128 is provided between detector 124 and tee connector 126 for regulating fluid communication therebetween.

Trap 122 is comprised of an elongated column of the porous layer open tubular (PLOT) type. PLOT column 130 has an inside coating of a stationary phase material such as aluminum oxide (AlO) which adsorbs a group of gases referred to as NMOG, while permitting a second group of gases including methane and so-called permanent gases (nitrogen, oxygen, carbon dioxide) to pass through the column. Other PLOT column configurations and stationary phases could also be used, including the following commercially available products: PoraPLOT Q™, PoraPLOT U™, and CarboPLOT™ columns. Column 130 is surround by heater tube 132 which is connected to an electric heater circuit 134 which permits the temperature of column 130 to be rapidly increased for the desorption of trapped NMOG, as will be described in more detail. The opposite end of column 130 is connected to second branch 113 which includes fluid restrictor 138 which like restrictor 114, serves to control fluid flow rates. Carrier gas source 116 is connected at the connection 136 between column 130 and restrictor 138 through on/off valve 140. Vacuum source 142 is connected through on/off valve 144 between restrictor 138 and detector 146 at tee connector 148. Detector 146 like detector 124, is preferably an FID. Detector 146 is needed only when a quantitative evaluation of the methane group is desired. Where such a measurement is not needed, tee connector 148 can be vented to atmosphere.

An example of analysis system 110 would employ the following specific components and parameters for the analysis of internal combustion engine exhaust gases:

| ELEMENT NUMBER | ELEMENT NAME | SPECIFICATION/ PARAMETER |
|---|---|---|
| 114 and 138 | Restrictor | 0.1 mm fused silica glass capillary tubing, 30 cm long |
| 116 | Carrier Gas Source | Hydrogen |
| 120,128,140,144 | Valves | Low dead-volume On/off solenoid controlled valves of the type commonly used in gas chromatography instruments |
| 130 | Column | 15 cm long fused silica glass capillary, 0.32 mm ID with AlO stationary phase coating |
| 132 | Heater Tube | Stainless Steel Tubing |
| 134 | Heater Circuit | Capacitive-Discharge circuit as described in U.S. Pat. No. 5,096,471, herein incorporated by reference |

Operation of analysis system 110 will now be described with particular reference to the Figures. At the beginning of an analysis procedure, exhaust gas or another gas sample for evaluation is delivered to sample inlet 112 while valves 120, 128, and 140 are closed, and valve 144 is open. Vacuum source 142 draws the sample into first branch 111 and toward column 130. As soon as the sample has passed beyond tee connection 118, the vacuum source 142 is disconnected by closing valve 144. Thereafter, the carrier gas source 116 drives the sample into column 130 by opening valve 120.

The temperature of column 130 is set to allow the methane group of gases to pass through with very little retention while adsorbing the NMOG group onto the stationary phase of column 130. Accordingly, column 130 acts as a separation column for the methane and NMOG groups. In order to provide separation, the temperature of column 130 needs to be held at a "trapping" temperature within a predetermined range, which is believe to extend from ambient temperatures (eg. 20° C.) to sub-ambient temperatures down to −100° C. and perhaps lower, depending on the particular configuration of system 110 and especially column 130. Where an ambient trapping temperature is used, the trapping temperature can be provided by exposing column 130 to ambient air. Where cooler trapping temperatures are needed, a bath of cooled water or a cold gas (eg. nitrogen) can be used to cool column 130.

Figure 5:
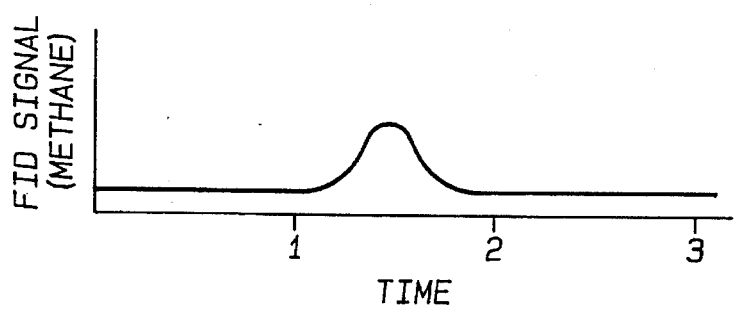
FIG. 5 is a representative chromatogram from a detector providing a measurement of methane concentration using the instrument of FIG. 4.
Figure 6:
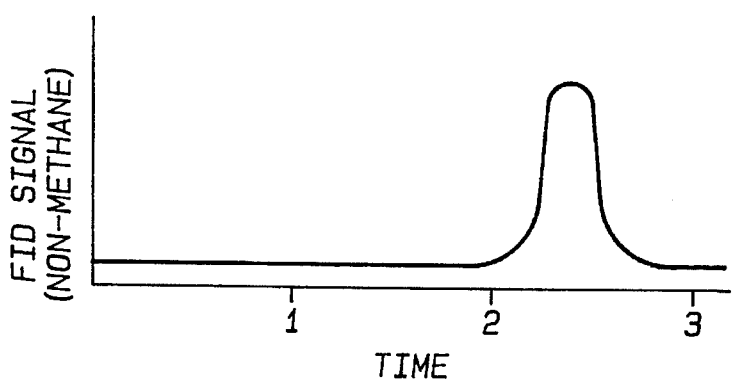
FIG. 6 is a representative chromatogram from a detector providing a measurement of NMOG concentration using the instrument of FIG. 4.

Once the methane gas group has passed through column 130 beyond tee connection 136, carrier gas source 116 is applied to tee connection 136 by opening valve 140, while valve 120 remains open. This action produces a splitting of the flow of carrier gas at tee connection 136 in which a fraction of the carrier gas continues to drive the methane gas group through restrictor 138 and through FID 146 where its presence is detected and a quantitative measurement is provided. FIG. 5 provides a representative output from FID 146 which can be integrated to obtain a measure of the concentration of the methane gas group. The balance of carrier gas 116 flows into column 130 which causes the direction of fluid flow through the column to be reversed; namely, toward FID 124. Simultaneous with the flow reversal, heater circuit 134 is activated, causing the temperature of column 130 to be increased rapidly to a desorption temperature above the trapping temperature. The desorption temperature would be above ambient (20° C.) and may be 200° C. or higher, depending on the characteristics of system 110. This temperature increase causes the NMOG group components retained by column 130 to be desorbed. By opening valve 128, the NMOG components which are desorbed pass to FID 124 where they are detected and integrated. FIG. 6 provides a representative output of the desorbed NMOG group from FID 124. The flow reversal through column 130 also provides backflushing for clearing the column for a subsequent sample evaluation. After integration at FID 124, valves 120, 128 and 140 are again closed, enabling the next sample to be introduced into the system.

Use of a PLOT column instead of a packed column can reduce the time necessary to bring the column to an adsorption temperature, and reduces the time necessary for the column to reach a desorption temperature, therefore decreasing desorption time. When instructing a packed column with a plurality of internally contained spherical beads, the spherical point contact between beads provides a thermal pathway which is inherently poor at conducting heat transfer between adjacent contacting spheres. Poor heat transfer substantially decreases the cycle time during adsorption/ desorption cycles when using such an instrument in repeatedly detecting constituents in a gas sample. Furthermore, a packed column has a substantially increased surface area and likewise requires a substantially larger gas sample size.

As a further consequence of the increased desorption rates provided when using a PLOT column in conjunction with this invention, the FID produces a signal which is compressed, and typically provides a compression pulse with a base bandwidth of 10 milliseconds. The quantity measured by the FID has a gaussian type plug distribution which is totally bounded within that time frame.

Furthermore, developmental tests indicate it is necessary to utilize a PLOT column having a maximum length of 30 cm. Additionally, the carrier gas velocity shall be in the range of 100 cm per/sec., and is preferably higher. Finally, a heating rate for such a PLOT column is on the order of 100,000° C./sec. It has also been observed that use of such a PLOT column with the backflush technique of this invention significantly reduces cycle times since such higher boiling point components in a gas sample significantly affect cycle times, and such higher boiling point components are trapped generally sooner in the PLOT column adjacent its inlet end. Therefore, when desorbing the PLOT column with a backflush technique, such trapped higher boiling point components travel over a shorter distance when desorbing them in a backflush direction. It is finally noted that the techniques of this invention are utilized for bulk quantity analysis and not for speciation of individual components.

A final observation indicates typical trapping times when utilizing this alternative variation of the invention on the order of one to two seconds. However, such trapping times are inter-related to the length of the PLOT trap.

While the above description constitutes the preferred embodiments of the present invention, it will be appreciated that the invention is susceptible of modification, variation and change without departing from the proper scope and fair meaning of the accompanying claims.

I claim:

1. An analysis system for a gaseous sample, the system providing a measurement of the concentration of said non-methane organic gases group and the concentration of said methane gases group, said system comprising:

means for providing a source of a gaseous sample including a non-methane organic gases group which excludes methane and a methane gases group including methane;

a metal capillary tube trap for trapping a first portion of the non-methane organic gases group of the gaseous sample and passing a remainder of the gaseous sample including the methane gases group and a remainder portion of the non-methane organic gases group;

a porous layer open tubular trap arranged downstream of said metal capillary tube trap for receiving the passed remainder of the gaseous sample, trapping the remainder portion of the non-methane organic gases group and passing the methane gases group;

temperature control means for selectively controlling the temperature of said metal capillary tube trap and said porous layer open tubular trap, said temperature control means causing said metal capillary tube trap to thermally trap said first portion of the non-methane organic gases group by adsorption at a first trapping temperature during an adsorption phase and desorbs said first portion of the non-methane organic gases group at an elevated first desorption temperature during a desorption phase, and causing said porous layer open tubular trap to thermally trap said remainder portion of the non-methane organic gases by adsorption at a second trapping temperature during said adsorption phase and desorbs said trapped remainder portion of the non-methane organic gases group at an elevated second desorption temperature during said desorption phase;

fluid circuit means for causing the gaseous sample to flow through said metal capillary tube trap and second porous layer open tubular trap in a first direction during said adsorption phase and thereafter causing the desorbed first portion of the non-methane organic gases group to flow in a second opposite direction through said metal capillary tube trap during said desorption phase and causing the desorbed remainder portion of the non-methane organic gases group to flow in the first direction through said porous layer open tubular trap during said desorption phase;

first detector means operably connected to said metal capillary tube trap for measuring a concentration of said first portion of the non-methane organic gases group flowing in the second direction after said first portion of the non-methane organic gases group is desorbed from said metal capillary tube trap; and second detector means operably connected to said porous layer open tubular trap for measuring a concentration of the methane gases group passed through said porous layer open tubular column and a concentration of said remainder portion of the non-methane organic gases group desorbed from said porous layer open tubular trap.

2. An analysis system according to claim 1 wherein said first detector means comprises a first flame ionization detector receiving said first portion of the non-methane organic gases group passed from said metal capillary tube trap in said second direction.

3. An analysis system according to claim 2 wherein said second detector means comprises a second flame ionization detector receiving the methane gases group passed through the porous layer open tubular trap, when at said second trapping temperature, where the concentration of the methane gases group is measured and further receiving the remaining desorbed remainder portion of the non-methane organic gases group desorbed from the porous layer open tubular trap.

4. An analysis system according to claim 1 wherein said temperature control means includes heater means having an electrical resistance heater responsive to control commands for thermal regulating the temperature of said metal capillary tube trap between said first trapping temperature and said first desorption temperature.

5. An analysis system according to claim 1 wherein said temperature control means includes a heater means having an electrical resistance heater responsive to control commands for thermal regulating the temperature of said porous layer open tubular trap between said second trapping temperature and said second desorption temperature.

6. An analysis system according to claim 1 wherein said metal capillary trap tube and said porous layer open tubular trap have a maximum combined length of 30 centimeters, and the remainder portion of the non-methane organic gases group desorbed from said porous layer open tubular trap is displaced therethrough by a carrier gas having a minimum velocity of 100 centimeters per second.

* * * * *